United States Patent [19]
Usher et al.

[11] Patent Number: 5,827,474
[45] Date of Patent: Oct. 27, 1998

[54] APPARATUS AND METHOD FOR MEASURING THE DEPTH OF MOLTEN STEEL AND SLAG

[75] Inventors: John D. Usher, Beaver Falls; Robin A. Sommers, Moon Township, both of Pa.

[73] Assignee: Vesuvius Crucible Company, Wilmington, Del.

[21] Appl. No.: 779,008

[22] Filed: Jan. 2, 1997

[51] Int. Cl.$^6$ .................................................. C21D 11/00
[52] U.S. Cl. ............................ 266/44; 266/94; 73/304 R
[58] Field of Search ................................. 266/87, 78, 90, 266/94, 99, 44; 73/304 R

[56] References Cited

U.S. PATENT DOCUMENTS

| | | | |
|---|---|---|---|
| 3,663,204 | 5/1972 | Jungwirth | 266/94 |
| 4,150,974 | 4/1979 | Kemlo | 266/94 |
| 4,365,788 | 12/1982 | Block | 266/87 |
| 4,721,533 | 1/1988 | Phillippi et al. . | |
| 5,071,258 | 12/1991 | Usher et al. . | |
| 5,361,825 | 11/1994 | Lax et al. . | |
| 5,375,816 | 12/1994 | Ryan et al. . | |
| 5,549,280 | 8/1996 | Kings et al. . | |
| 5,569,845 | 10/1996 | Butcher et al. . | |

FOREIGN PATENT DOCUMENTS

| | | |
|---|---|---|
| 0 080 965 | 10/1982 | European Pat. Off. . |
| 0 459 049 | 12/1991 | European Pat. Off. . |
| 1958224 | 5/1971 | Germany . |
| 3037658 | 5/1982 | Germany . |

OTHER PUBLICATIONS

PCT International Search Report.

*Primary Examiner*—Scott Kastler
*Attorney, Agent, or Firm*—Sixbey Friedman Leedom & Ferguson; Thomas W. Cole

[57] ABSTRACT

Both an apparatus and method for measuring the depth of slag and molten metal contained in a tundish, ladle, electric furnace, or other vessel is provided. The apparatus includes a voltmeter for comparing the electrical potential of the steel, the slag-steel interface, and the air-slag interface to a ground potential, in combination with a probe member formed from a conductive material. The probe member has a proximal end that is electrically connected to the voltmeter, and a distal end movable between the vessel floor and one or the other of the interfaces. The apparatus further includes an articulated arm for positioning the distal end of the probe member in the vessel and across the molten metal so that it traverses at least one of the other two interfaces. The depth of the molten metal or slag is determined by noting differences in the electrical potential detected by the voltmeter while monitoring the vertical position of the distal end of the probe member in the vessel. The probe member may be formed from an electrically conductive ceramic material, and may simultaneously take the form of a protector tube for another probe. Alternatively, the probe may take the form of the stopper rod normally used to modulate the flow of liquid steel out of the ladle, tundish, or other vessel.

17 Claims, 2 Drawing Sheets

APPARATUS AND METHOD FOR MEASURING THE DEPTH OF MOLTEN STEEL AND SLAG

BACKGROUND OF THE INVENTION

This invention relates to both an apparatus and method for measuring the depth of molten steel and slag in vessels used in steel refining, and is specifically concerned with the use of a vertically-movable probe member formed from a conductive ceramic material in combination with a voltmeter for detecting depth-wise the location of the interfaces between steel and slag, and slag and air.

Techniques for measuring the depth of molten steel covered by a layer of slag in a tundish or ladle are known in the prior art. Such techniques find particular utility in facilities designed for the continuous casting of a steel product. Continuous casting facilities generally comprise a casting mold, a bathtub-shaped tundish disposed above the mold and having an outlet nozzle for providing a modulated flow of molten steel into the mold, and a larger vessel known as a ladle for constantly refilling the tundish with molten steel. In both the tundish and the ladle, a layer of molten, non-metallic material known as slag is present over the upper surface of the molten steel. Such slag is formed from a mixture of the impurities separated from the metal during the refining operation and flux chemicals which are added during the refining process. The resulting layer of slag over the upper surface of the molten steel serves the useful purposes of regulating the percentage content of alloy additives in the steel, isolating the molten steel from ambient oxygen, and thermally insulating it so that it remains in a molten state until poured into the mold.

Periodically, the tundish in such facilities must be replaced due to the erosion of the refractory lining within the tundish vessel. Such a tundish replacement operation is known as a "tundish fly" in the art. During the tundish fly, it is desirable to drain out as much of the molten steel as possible to avoid unnecessary wastage and reclamation operations. Unfortunately, if any of the molten slag is allowed to flow through the outlet nozzle of the tundish into the continuous casting mold, the resulting quality of the steel will be seriously degraded. Worse yet, the entry of a significant amount of such slag into the mold could result in an explosive reaction which could jeopardize the lives of the steelworkers, and cause severe damage to the steel refining facilities. It is therefore critical that the depth of molten steel in the tundish be carefully monitored during the draining of the tundish so that a maximum amount of steel is drained without the entry of slag into the mold.

The simplest prior art method for determining the depth of molten steel in a tundish during draindown is the visual observation of the level of the slag in the tundish vessel as molten steel is poured into the mold. If the operator of the facility knows the approximate thickness of the layer of slag over the steel, the depth of the molten steel within the vessel can be roughly estimated by observing where the top of the slag layer is relative to the depth of the tundish vessel. But, such a method based upon visual estimations is necessarily inaccurate. Another simple prior art technique utilizes a lollipop-shaped "slag stopper" device comprising a refractory ball attached to a calibrated length of steel tube. The refractory ball floats at the slag-metal interface with the tube extending upwardly. The tube is indexed against a reference point, typically the tundish cover. When the stopper tube falls to a prescribed point the drawing of the tundish is shut off. However, the effectiveness of this technique is dependent upon a soft slag layer and a dimensionally stable tundish cover. Hence such a technique is not completely reliable. Also known are steel depth measuring devices which employ coils designed to generate eddy currents in the molten steel. The coil impedance changes substantially depending upon whether the fluctuating magnetic field generated by the coil interacts with the steel or the slag. Hence, the location of the steel-slag interface may be inferred as a function of measured coil impedance. While such devices may be able to measure the level of molten steel more accurately than visual techniques, they still provide only an approximation of the depth of the molten steel. Additionally, they are capital-intensive devices which must be constantly maintained in calibration.

The lack of accuracy associated with the depth determining methods and devices of the prior art necessarily causes the operators of such continuous casting facilities to stop the draindown of steel during a tundish fly when the estimated steel level is between 18 and 24 inches from the bottom of the tundish. While such a conservative approach generally insures that no slag will enter the mold, it also necessarily results in between 5 and 10 tons of steel being wasted at a cost of approximately $200.00 per ton.

The applicants have also observed that there is a need for accurately measuring not only the depth of the layer of steel in such casting facilities, but also the depth of the layer of slag. Such a need arrives after the steel has been initially poured into the ladle and the ladle has been moved into the ladle treatment station of the facility. Here, a dosage of alloy chemicals known as a "trim addition" are added to the raw steel and thoroughly mixed therein to bring the final steel product within the alloy specifications of the desired final product. After the trim addition has been mixed into the molten steel, the steel is immediately analyzed in order to confirm that its composition meets alloy specifications. If it does not, another trim addition is made in order to bring the final steel product within specifications.

Because of the time, effort, and expense associated with each trim addition, it is highly desirable that only one such trim addition be made. However, because of the chemical reactivity of the layer of slag that overlies the raw steel delivered into the ladle treatment station, some of the chemicals in the trim addition become compounds in the slag instead of alloy components in the steel. If the thickness of the slag is accurately known, then the amount of alloy additives in the trim addition can be adjusted to compensate for the loss of such chemicals through their reaction with the slag. However, because of inherent variabilities in the amount of slag that is transferred to the ladle vessel from the refining vessel, there are always variabilities in the thickness of the slag layer that ultimately overlies the molten steel in the ladle. This problem has been recently exacerbated by the use of calcium carbide in such refinement facilities. While the addition of calcium carbide advantageously reduces some of the uncertainties associated with the loss of alloy chemicals in the slag by substantially neutralizing the chemical activity of the slag, it unfortunately causes the slag to foam to a greater or less degree. Because such foaming slag is still reactive enough to affect the final balance of alloy chemicals that become part of the refined steel, it would be highly desirable if the system operator could easily determine both the thickness and density of the foaming slag layer created by the calcium carbide. Such knowledge would largely obviate the need for a second trim addition of alloy chemicals designed to "tweak" the final composition of the steel into the desired specifications.

Clearly, there is a need for a device for determining the depth of molten steel and slag in a refinement vessel in order both to minimize the amount of steel wasted during a tundish fly operation, and obviate the need for a second trim addition at a ladle treatment station. Ideally, such a device would be reliable, and simple and rugged in construction, and inexpensive to manufacture and to use. Finally, it would be desirable if such a device could be easily installed and used in connection with preexisting equipment so as to minimize the effort and expense associated with installation.

SUMMARY OF THE INVENTION

Generally speaking, the invention is both an apparatus and method for measuring slag and molten metal depths in a tundish, ladle, electric furnace, or other metallurgical vessel that overcomes or at least ameliorates all of the aforementioned shortcomings associated with the prior art.

The apparatus of the invention comprises a voltmeter for comparing the electrical potential of the molten metal in the vessel, the interface between the molten metal and slag in the vessel, and the interface between the slag and the ambient air to a ground potential. The apparatus further comprises a probe member that is formed at least in part from an electrically conductive material. The probe member has a proximal end electrically connected to the voltmeter, and a distal end movable between the vessel floor and either of the two interfaces. Finally, the apparatus comprises a probe positioning assembly, which may include an articulated arm, for moving the distal end of the probe member through the molten steel in the vessel and across at least one of the interfaces. The probe positioning assembly includes a means for determining the vertical position of the probe member. The depth of molten steel or other metal in the vessel or the depth of the slag is determined by comparing differences in electrical potential detected by the voltmeter while noting the vertical position of the distal end of the probe member.

In one embodiment of the invention, the probe member is formed from an electrically conductive ceramic material, such as a mixture of 30% to 95% alumina, zirconia or magnesia and 5% to 50% graphite. Such ceramic material is preferably isostatically compressed in order to enhance its erosion-resistance. Advantageously, the probe member may take the form of an existing tube protector of the type used to house probes which measure other parameters of the molten steel, such as temperature or composition. When such a tube protector is used as the probe member, the positioning means may advantageously take the form of the manipulator arm that is normally used to move such a probe in its tube protector throughout the molten metal and slag. The "piggybacking" of the invention into an existing probe system advantageously minimizes the amount of extra components necessary to implement the apparatus of the invention.

Alternatively, the probe member may assume the form of the stopper rod that is normally used to modulate a flow of molten steel through the flow nozzle positioned at the bottom of the tundish, ladle, or other vessel containing the molten steel and slag. Such stopper rods are normally comprised of electrically conductive ceramic materials of the same basic types as the ones used to construct prior art protector tubes. Advantageously, the means for positioning the distal end of the combination stopper rod and probe member may be the same articulated arm used to reciprocally move the stopper rod incident to the modulation of the flow of steel. Again, such an arrangement minimizes the amount of extra components needed to implement the apparatus of the invention.

The apparatus may further comprise an impedance monitor connected in parallel across the voltmeter for determining the integrity of the voltage readings generated by the voltmeter. If the electrical connection between the probe member and the voltmeter should break during the operation of the apparatus, the voltmeter could still generate a spurious voltage based upon thermocouple effects of the conductors leading into the voltmeter. However, under such conditions, the impedance monitor would register an infinite impedance characteristic of an open circuit condition between the voltmeter and the probe member, which in turn would inform the system operator that the voltmeter readings were spurious. Alternatively, if a short circuit should occur between the probe member and a ground potential, the impedance monitor would dispel any voltage readings generated by the voltmeter as spurious, since it would immediately register that a completely closed circuit condition existed.

The invention further includes a method for determining the depth of molten steel or slag in a vessel by means of the previously described probe member and voltmeter that comprises the step of positioning the distal end of the probe member in the molten metal so that at least one of the interfaces between the molten metal and slag, or slag and air traverses the distal probe end while comparing differences in electrical potential sensed by the voltmeter, and determining the vertical position of the distal end upon each substantial change in measured potential.

In either case, the invention may be used to determine the level of molten steel or other metal in a tundish, ladle, electric furnace, or other vessel so that a maximum amount of the steel may be drained out of the vessel without the inclusion of unwanted slag deposits. Alternatively, the invention may be used to accurately measure the depth of the layer of slag covering the steel or other metal at a ladle treatment station in order to minimize the need for more than one trim addition of alloy chemicals.

BRIEF DESCRIPTION OF THE SEVERAL FIGURES

DETAILED DESCRIPTION OF THE PREFERRED EMBODIMENT

Figure 1:
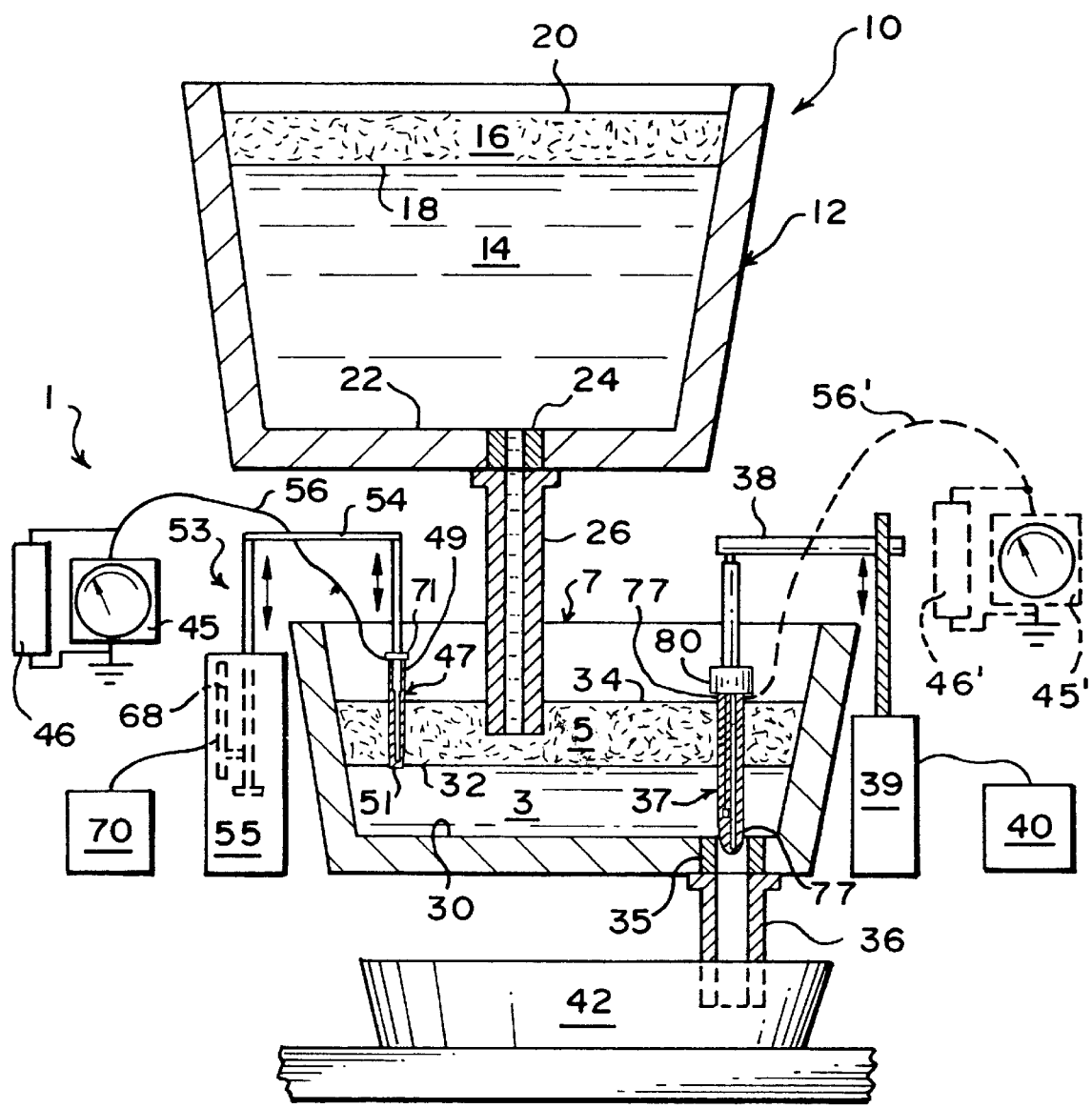
FIG. 1 is a schematic diagram of the steel and slag depth measuring device of the invention installed in the tundish of a continuous casting facility.

With reference now to FIG. 1, the steel and slag depth measuring device 1 of the invention is particularly useful for measuring the depth of either the molten steel 3 or the slag 5 in a tundish 7 or ladle vessel 12. However, before the specific structure and operation of the device 1 will be described, a brief description of the continuous casting facility 10 shown in FIG. 1 will be given so that the utility of the device 1 may be better appreciated.

A continuous casting facility 10 for molten steel generally comprises a relatively large ladle vessel 12 disposed over a smaller tundish vessel 7. Ladle 12 contains a reservoir of molten steel 14 covered by a layer of slag 16. In the ladle, the slag 16 serves to adjust the chemistry of the steel by both removing impurities, and modifying the percentage content of alloying metals and other chemicals. Slag 16 also thermally insulates the molten steel 14, and isolates it from ambient oxygen. Between the upper surface of the molten steel 14 and layer of slag 16 lies a metal-slag interface 18. Similarly, a slag-air interface 20 lies between the upper surface of the layer of slag 16 and the ambient atmosphere. Finally, the ladle 12 has a bottom wall 22 that includes an outlet nozzle 24 with an integrally formed shroud 26 for admitting a flow of molten steel into the tundish 7. While the device 1 of the invention is shown as being installed in the tundish 7, it could also be installed in the ladle 12. So installed, the device 1 could be advantageously used to measure not only the depth of the layer of slag 16, but also its density (in the case of foamed slags) which in turn would assist the facility operator in controlling the ultimate chemical composition of the steel poured from the ladle 12 into the tundish 7.

Like the ladle 12, the tundish 7 includes a bottom wall 30, a metal-slag interface 32, and a slag-air interface 34. A nozzle 35 is mounted onto the bottom wall 30 for admitting a flow of molten steel into a continuous casting mold 42 via a shroud 36 located beneath the tundish 7. A vertically movable stopper rod 37 attached to an articulated arm 38 modulates the flow of molten steel 3 into the continuous casting mold 42. The articulated arm 38 is reciprocally moved via an arm moving assembly 39 which may include a vertical movement display 40 for indicating the vertical position of the distal end of the stopper rod 37. Movement display 40 is preferably implemented by state-of-the-art electronic data storage and computing circuitry. While the stopper rod 37 and associated components form no part of the instant invention, it should be noted that the invention may be conveniently "piggybacked" to the rod 37 in a manner which will be described in more detail hereinafter.

The device 1 of the invention comprises a voltmeter 45 in combination with an impedance monitor 46 connected in parallel thereto. The device 1 further includes a probe member 47 having an elongated body 48 formed from a conductive ceramic material, such as a ceramic oxide mixed with graphite. In the preferred embodiment, the probe member 47 is comprised of between 30% and 95% alumina, zirconia, magnesia, or some other ceramic oxide intermixed with between 5% and 50% graphite or other form of carbon. The ceramic composition forming the elongated body 48 is preferably isostatically pressed in order to render the resulting composition more erosion resistant to the effects of molten steel. The elongated body includes a proximal end 49 generally disposed above the layer of slag 5, and a distal end 51 for sensing the bottom wall 30, metal-slag interface 32, and slag-air interface 34. The device 1 further includes a probe positioning assembly 53 for positioning the probe member 47 with respect to said bottom wall 30, so that it traverses the steel-slag interface 32, and slag-air interface 34. The probe moving assembly 53 is formed from an articulated arm 54 which is moved vertically via an arm moving assembly 55. A flexible electrical conductor 56, which may be a temperature resistant wire, interconnects the proximal end 49 of the probe member 47 to the input of the voltmeter 45.

Figure 2:
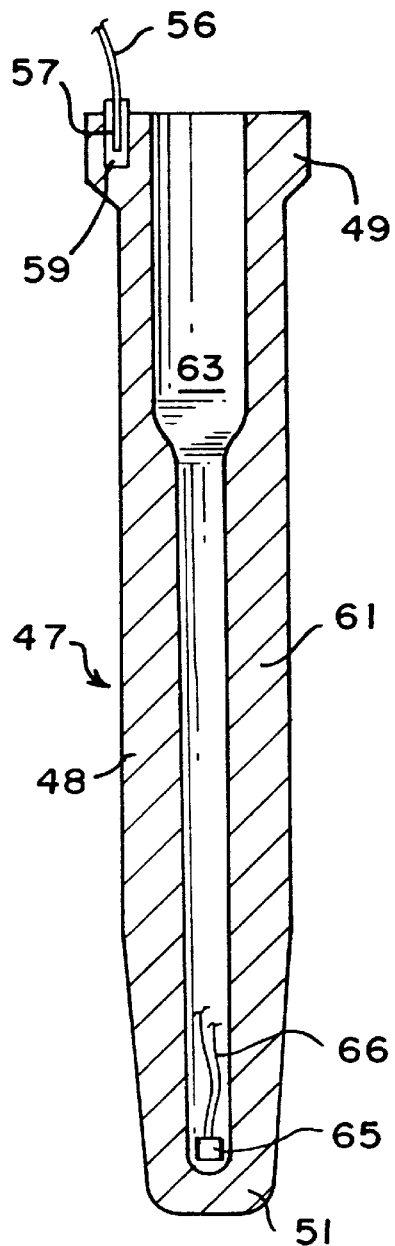
FIG. 2 is an enlarged, cross-sectional side view of the probe member used in the device of FIG. 1, wherein the probe member is formed from a ceramic protector tube of the type used to house one or more probes of other types that form no part of the instant invention.

With reference now to FIG. 2, one end 57 of the flexible electrical conductor 56 may be secured to the proximal end 49 of the probe member 47 via an electrically conductive, refractory mortar 59. In this first preferred embodiment of the invention, the probe member 47 is in fact a protector tube 61 having a hollow interior 63 as shown. Hollow interior 63 advantageously houses a probe 65, such as a thermocouple, having a function that is completely unrelated to the device 1 of the invention. Lead wire 66 from the probe 65 is connected to sensing circuitry (not shown) for measuring and displaying an output signal generated by such a probe 65. Such protector tubes 61 and the probe moving assembly 53 for vertically moving them through the molten steel 3 in a tundish 7 are known in the prior art and per se form no part of the invention. An example of such a protector tube and tube moving assembly is the Accumetrix® system manufactured and sold by the Vesuvius Crucible Company located in Wilmington, Del. Such a protector tube is disclosed in U.S. Pat. No. 4,721,533, assigned to the Vesuvius Crucible Company, the entire disclosure of which is expressly incorporated herein by reference. The positioning assembly 53 normally sold in connection with such protector tubes advantageously includes an electronic movement sensor 68, which may be a slide resistor mechanically linked to the articulated arm 54. Such systems further include a movement display 70 for receiving the electric signals generated by the movement sensor 68 and converting them into a vertical distance. Like the previously-mentioned movement display 40, display 70 is preferably implemented by state-of-the-art data storage and computing circuitry. The advantage of "piggybacking" the device 1 of the invention to such a protector tube 61 and probe positioning assembly 53 is that only a voltmeter 45, and impedance monitor 46, and electrical conductor 56 are necessary to complete the invention. The protector tube 47 is normally formed from an electrically conductive ceramic material. Accordingly, no structural modifications are necessary, other than the aforementioned electrical connection of the tube 47 to the conductor 56, and the use of an insulatory cap 71 to mechanically connect the tube 47 to the articulated arm 54 so that the tube 61 does not become electrically grounded. Such an unwanted grounding of the protector tube 61 would prevent the voltmeter from accurately measuring and displaying the electric potential associated with the molten steel 3, the steel-slag interface 32, and the air-slag interface 34.

Figure 3:
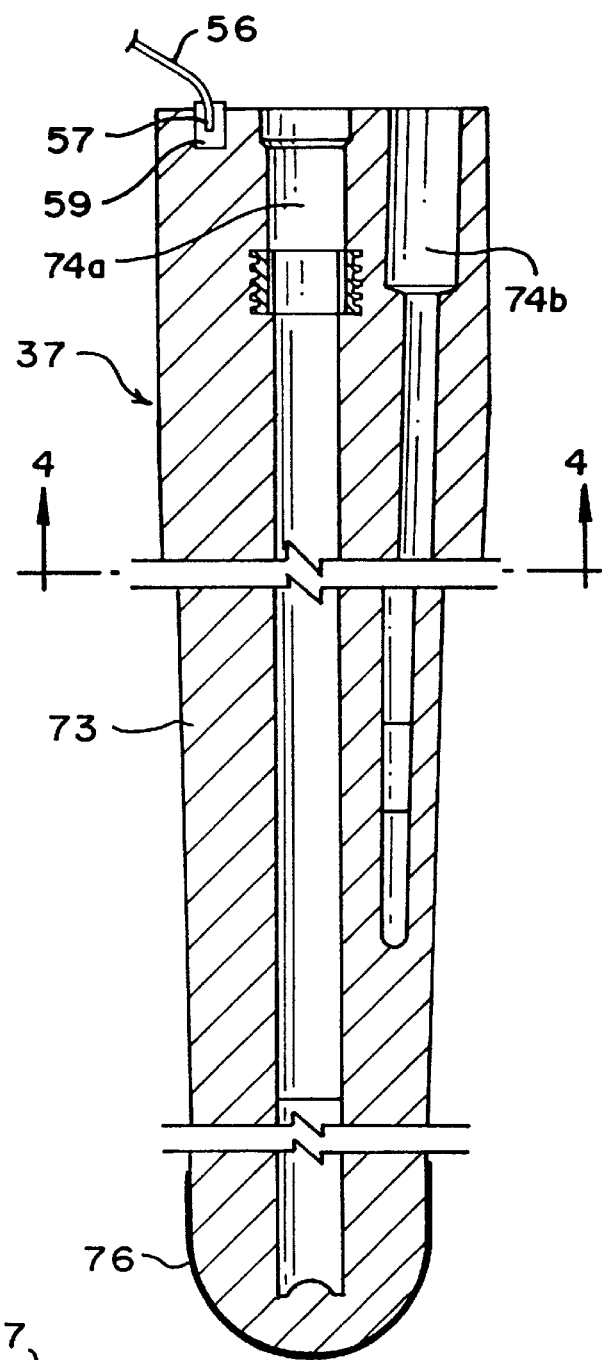
FIG. 3 is a cross-sectional side view of a stopper rod which may likewise form the probe member of the device of the invention.
Figure 4:
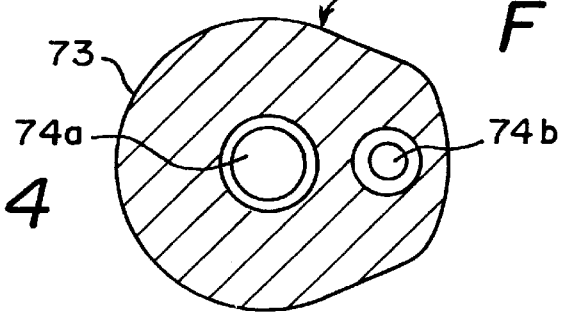
FIG. 4 is a cross-sectional plan view of the stopper rod of FIG. 3 along the line 4—4.

With reference now to FIGS. 1, 3, and 4, the stopper rod 37, articulated arm 38, arm moving assembly 39, and vertical movement display 40 may likewise be used as components of the device 1, so long as the stopper rod 37 is formed from a conductive material, such as a graphite containing ceramic. Such a stopper rod 37 likewise includes an elongated body 73 which may have elongated passages 74a,b for the blowing of an inert gas such as argon into the molten steel, and for the housing of other probes having nothing to do with the invention respectively. Such a stopper rod has a distal end 75 that is typically coated with a stick-resistant coating 76 that is resistant to the accumulation of molten steel. Stopper rod 37 further includes a proximal end 77 which may be connected to a flexible conductor 56' which leads to the input of a voltmeter 45' to which an impedance monitor 46' is connected. However, if one chooses to use stopper rod 37 and attendant arm moving assembly 39 as components of the device 1, it is necessary that the stopper rod 37 be mechanically connected to the articulated arm 38 via an insulatory cap 80 for the same reasons given with respect to the protector tube 61 used as the probe member 47 in the first embodiment.

In one mode of operation, the operator of the device 1 determines the depth of the layer of molten steel 3 in the tundish 7 by engaging the distal end 51 of the probe member 47 against the bottom wall 30 of the tundish 7, and noting its vertical position via movement display 70. Next, the probe member 47 is slowly vertically raised until the voltmeter 45 registers a substantial change in electrical potential. Such a change will occur when the distal end 51 of the probe member 47 engages the metal-slag interface 32. At this time, the vertical position of the probe member 47 is again noted via the movement display 70. The depth of the layer of molten steel 3 within the tundish 7 may then be inferred. If the operator of the device 1 wishes to further know the depth of the layer of slag 5, the probe member 47 may again be raised until the voltmeter 45 registers a further substantial change in electrical potential. Such a change will occur when the distal end 51 engages the air-slag interface 34. The vertical position of the probe member 47 is again noted via the movement display 70. The slag depth may then be inferred by subtracting the difference between the vertical position between the metal-slag interface 32 and the slag-air interface 34. Of course, the same procedure could be used if the device 1 were installed in the ladle vessel 12. In such a case, if the slag layer 16 had been foamed as a result of the addition of calcium carbide to the layer of steel 14, the density as well as the depth of the slag 16 could be inferred, since the potential registered by the voltmeter 45 would vary in accordance with the amount of foaming.

All throughout this procedure, the impedance monitor 46 monitors changes in impedance between the flexible electrical conductor 56, and a ground potential. The integrity of the reading may then be checked utilizing the same techniques disclosed and claimed in U.S. Pat. No. 5,549,280 (assigned to Vesuvius Crucible Company), the entire specification of which is incorporated herein by reference. The exact same operating procedure may be used in the second embodiment of the invention, the only difference being that some compensation must be made for the fact that the distal end 76 of the stopper rod 37 is not necessarily at the same level as the bottom wall 30 when the stopper rod 37 is seated within the flow nozzle 35. For example, if it is known that the distal end 76 is 10 centimeters below the bottom wall 30 of the vessel 7 when in a seated position, then 10 centimeters in vertical distance must be subtracted from the vertical distance between the distal end 76 and the metal-slag interface 32 when the stopper rod 37 is vertically moved upwardly via the arm 38 and the arm moving assembly 39.

While this invention has been described with respect to two preferred embodiments, various equivalences, modifications, additions and alternate embodiments will become apparent to persons in the art. For example, while a voltmeter is used in the various embodiments to compare the electrical potential of the slag or molten steel to a ground potential, any electronic circuit capable of measuring or sensing an electrical potential with respect to any reference point (ground or otherwise) could be used instead. While the probe member of the apparatus has been described in terms of an elongated body formed from an electrically conductive ceramic material, this member may be formed from a metallic material that has a melting point above that of the molten steel or other metal being refined. While the positioning means for the probe member has been described in terms of an articulated arm of the type used to move the protector tube of a temperature probe or the stopper rod of a tundish, it is evident that any mechanism capable of generating a vertical component of motion between an end of the probe member and the layer of molten steel or slag could also be used. And, while the operation of the invention has been described in manual terms, such operation could easily be automated via state-of-the-art computer technology so as to obviate the need for the previously described manual reading steps. All such equivalences, additions, modifications, and variations of the invention which are within present technology, and which will become available through future technology are within the scope of this invention, which is limited only by the claims appended hereto.

What is claimed:

1. Apparatus for measuring slag layer depths and molten metal depths in a vessel containing molten metal covered by a layer of slag, comprising:

means for comparing an electrical potential of said molten metal and said molten slag to a reference potential;

a probe member including a protector tube formed from an electrically conductive ceramic material for housing a probe having a function unrelated to slag or metal depth measurement, said tube having a proximal end in electrical communication with said potential comparing means and a distal end movable across one of said depths, and means for positioning said distal end of said protector tube within said vessel such that said distal end traverses at least one of said depths and for measuring a vertical position with respect to said vessel such that a depth of molten metal or slag is measured by comparing differences in electrical potential sensed by said potential comparing means during said traversal.

2. The apparatus for measuring slag and molten metal depths as defined in claim 1, wherein said protector tube is formed from a mixture comprising graphite and one of the group consisting of alumina, zirconia, and magnesia.

3. The apparatus for measuring slag and molten metal depths as defined in claim 1, wherein said potential comparing means is a voltmeter.

4. The apparatus for measuring slag and molten metal depths as defined in claim 3, further comprising an impedance monitoring means connected in parallel across said voltmeter for determining the integrity of readings of said voltmeter.

5. The apparatus for measuring slag and molten metal depths as defined in claim 1, wherein said positioning means includes an articulated arm assembly connected to said probe member for reciprocally moving said member, and means for measuring said vertical component of movement.

6. The apparatus for measuring slag and molten metal depths as defined in claim 5, further comprising means for electrically insulating said connection between said articulated arm assembly and said probe member.

7. Apparatus for measuring slag layer depths and molten steel depths in a vessel containing molten steel covered by a layer of slag, comprising:

a voltmeter for comparing, to a ground potential, an electrical potential of molten steel to a slag-molten steel interface, and to an air-slag interface;

a probe member including a protector tube formed from an electrically-conductive, graphite-containing ceramic material for housing a probe for measuring a temperature or chemical parameter of said steel or slag, said tube having a proximal end in electrical communication with said voltmeter and a distal end relatively movable with respect to said interfaces, and means for positioning said distal end of said protector tube within said vessel such that said distal end moves across at least one of said interfaces and for measuring a vertical distance associated with said positioning such that a depth of molten steel or slag is measured by comparing differences in electrical potential detected by said voltmeter during said movement.

8. The apparatus for measuring slag and molten metal depths as defined in claim 7, wherein said means for positioning said distal end moves said distal end of said protector tube across at least one of said interfaces, and measures a vertical component of such movement such that a depth of molten steel or slag is measured.

9. The apparatus for measuring slag and molten metal depths as defined in claim 7, wherein said probe member is formed by isostatically pressing a mixture comprising a ceramic oxide mixed with graphite.

10. The apparatus for measuring slag and molten metal depths as defined in claim 7, further comprising an impedance monitoring means connected in parallel across said voltmeter for determining the integrity of readings of said voltmeter.

11. The apparatus for measuring slag and molten metal depths as defined in claim 8, wherein said positioning means includes an articulated arm that functions both to reciprocally move said probe member for slag and metal depth measurements, and to move said protector tube of said probe member for temperature or chemical parameter measurements, said positioning means also including means for electronically measuring a vertical component of said movement.

12. The apparatus for measuring slag and molten metal depths as defined in claim 11, wherein said electronic measuring means includes a slide resistor.

13. Apparatus for measuring slag layer depths and molten metal depths in a vessel containing molten metal covered by a layer of slag, comprising:

a voltmeter for comparing an electrical potential of said molten metal and said molten slag to a reference potential;

a probe member including a protector tube formed from an electrically conductive ceramic material containing graphite for housing a probe for measuring a temperature or chemical parameter of said molten metal, said tube having a proximal end in electrical communication with said voltmeter and a distal end movable across one of said depths, and an articulated arm for moving said distal end of said probe member and said protector tube across at least one of said depths for both measuring a vertical component of such movement such that a depth of molten metal or slag is measured by comparing differences in electrical potential sensed by said voltmeter as said distal end of said probe member is moved, and for manipulating said probe to measure said temperature or chemical parameter.

14. A method for measuring slag layer or molten metal depths in a vessel containing molten metal covered by a layer of slag by a probe member formed from an electrically conductive ceramic material containing graphite and having a movable distal end, and a proximal end in electrical communication with a voltmeter for sensing and comparing an electrical potential of said molten metal or slag to a reference potential, comprising the step of:

moving said distal end of said probe member through a depth of said slag layer or said molten metal while comparing differences in electrical potential sensed by said voltmeter and while measuring a vertical component of said movement.

15. A method for measuring slag layer or molten metal depths in a vessel containing molten metal covered by a layer of slag by means of a probe member formed from an electrically conductive ceramic material containing graphite and having a distal end, and a proximal end in electrical communication with a means for comparing an electrical potential said probe member also including a protector tube for housing a probe having a function unrelated to slag or metal depth measurement of said molten metal, slag-metal interface and air-slag interface to a ground potential, comprising the steps of:

positioning said distal end of said probe member within said vessel;

determining a vertical distance between said probe end and a bottom of said vessel, and generating relative movement between said distal end of said probe member and at least one of said interfaces while comparing differences in electrical potential sensed by said comparing means such that a depth of said molten metal layer or said slag layer is determined.

16. Apparatus for measuring slag layer depths and molten metal depths in a vessel containing molten metal covered by a layer of slag, comprising:

means for comparing an electrical potential of said molten metal and said molten slag to a reference potential;

an impedance monitoring means connected in parallel across said voltmeter for determining the integrity of readings of said voltmeter;

a probe member formed from an electrically conductive ceramic material having a proximal end in electrical communication with said potential comparing means and a distal end movable across one of said depths; and means for positioning said distal end of said probe member within said vessel such that said distal end traverses at least one of said depths and for measuring a vertical position with respect to said vessel such that a depth of molten metal or slag is measured by comparing differences in electrical potential sensed by said potential comparing means during said traversal.

17. Apparatus for measuring slag layer depths and molten metal depths in a vessel containing molten metal covered by a layer of slag, comprising:

means for comparing an electrical potential of said molten metal and said molten slag to a reference potential;

a stopper rod formed from an electrically conductive ceramic material having a proximal end in electrical communication with said potential comparing means and a distal end movable across one of said depths; and means for positioning said distal end of said stopper rod within said vessel such that said distal end traverses at least one of said depths and for measuring a vertical position with respect to said vessel such that a depth of molten metal or slag is measured by comparing differences in electrical potential sensed by said potential comparing means during said traversal.

* * * * *